United States Patent [19]
Findeis et al.

[11] Patent Number: 5,817,626
[45] Date of Patent: Oct. 6, 1998

[54] MODULATORS OF BETA-AMYLOID PEPTIDE AGGREGATION

[75] Inventors: Mark A. Findeis, Boston; Howard Benjamin, Lexington; Marc B. Garnick, Brookline; Malcolm L. Gefter, Lincoln; Arvind Hundal, Brighton, all of Mass.; Laura Kasman, Athens, Ga.; Gary Musso, Hopkinton, Mass.; Ethan R. Signer, Cambridge, Mass.; James Wakefield, Brookline, Mass.; Michael J. Reed, Oak Ridge, Tenn.

[73] Assignee: Praecis Pharmaceuticals Incorporated, Cambridge, Mass.

[21] Appl. No.: 404,831

[22] Filed: Mar. 14, 1995

[51] Int. Cl.⁶ .................... A61K 38/17; C07K 1/113; C07K 14/47
[52] U.S. Cl. ................ 514/12; 530/324; 530/326; 530/345
[58] Field of Search ................ 514/12; 530/324, 530/325, 326, 345

[56] References Cited

U.S. PATENT DOCUMENTS

| | | | |
|---|---|---|---|
| 4,666,829 | 5/1987 | Glenner et al. | 530/806 |
| 5,231,170 | 7/1993 | Averback | 530/388.1 |
| 5,276,059 | 1/1994 | Caughey et al. | 514/647 |
| 5,338,663 | 8/1994 | Potter et al. | 435/4 |
| 5,358,934 | 10/1994 | Borovsky et al. | 514/17 |
| 5,369,009 | 11/1994 | Arceci et al. | 530/387.7 |
| 5,434,050 | 7/1995 | Maggio et al. | 530/839 |
| 5,464,821 | 11/1995 | Stig et al. | 514/18 |
| 5,470,951 | 11/1995 | Roberts | 530/330 |
| 5,523,295 | 6/1996 | Fasman | 514/63 |
| 5,559,209 | 9/1996 | Nishimoto | 530/326 |

FOREIGN PATENT DOCUMENTS

| | | |
|---|---|---|
| 0 554 887 A1 | 8/1993 | European Pat. Off. . |
| 0 641 861 | 3/1995 | European Pat. Off. . |
| WO 93/04194 | 3/1993 | WIPO . |
| WO 94/28412 | 12/1994 | WIPO . |
| WO 95/05394 | 2/1995 | WIPO . |
| WO 95/05604 | 2/1995 | WIPO . |

OTHER PUBLICATIONS

Barrow, Colin J. and Michael G. Zagorski (1991) "Solution Structures of β Peptide and Its Constituent Fragments: Relation to Amyloid Deposition" *Science* 253: 179–182.

Barrow, Colin J. et al. (1992) "Solution Conformations and Aggregational Properties of Synthetic Amyloid β–Peptides of Alzheimer's Disease: Analysis of Circular Dichroism Spectra" *J. Mol. Biol.* 225: 1075–1093.

Brown, Abraham M. et al. (1994) "Biotinylated and Cysteine–Modified Peptides as Useful Reagents for Studying the Inhibition of Cathepsin G" *Analytical Biochemistry* 217: 139–147.

Burdick, Debra et al. (1992) "Assembly and Aggregation Properties of Synthetic Alzheimer's A4/β Amyloid Peptide Analogs" *Journal of Biological Chemistry* 267(1): 546–554.

Chantry, Andrew et al. (1992) "Biotinyl Analogues of Amylin as Biologically Active Probes for Amylin/CGRP Receptor Recognition" *FEBS* 296(2): 123–127.

(List continued on next page.)

*Primary Examiner*—Jeffrey E. Russel
*Attorney, Agent, or Firm*—Lahive & Cockfield LLP; Guilio A. DeConti, Jr.; Catherine J. Kara

[57] ABSTRACT

Compounds that act to modulate the aggregation of natural β amyloid peptides (β-AP) are disclosed. The β amyloid modulators of the invention can promote β-AP aggregation or, more preferably, can inhibit natural β-AP aggregation. Furthermore, the modulators are capable of altering natural β-AP aggregation when the natural β-APs are in a molar excess amount relative to the modulators. Preferred β amyloid modulators comprise amino-terminally biotinylated β amyloid peptide compounds. Pharmaceutical compositions comprising the compounds of the invention, and methods of altering natural β-AP aggregation using the compounds of the invention, are also disclosed.

27 Claims, 1 Drawing Sheet

OTHER PUBLICATIONS

Clements, Angela et al. (1993) "Aggregation of Alzheimer's Peptides" *Biochemical Society Transactions* 22: 16S.

Come, Jon H. et al. (1993) "A Kinetic Model for Amyloid Formation in the Prion Diseases: Importance of Seeding" *Proc. Natl. Acad. Sci. USA* 90: 5959–5963.

Evans, Krista C. et al. (1995) "Apolipoprotein E Is A Kinetic But Not a Thermodynamic Inhibitor of Amyloid Formation: Implications for the Pathogenesis and Treatment of Alzheimer Disease" *Proc. Natl. Acad. Sci. USA* 92: 763–767.

Fabian, Heinz et al. (1993) "Comparative Analysis of Human and Dutch–Type Alzheimer β–Amyloid Peptides by Infrared Spectroscopy and Circular Dichroism" *Biochemical and Biophyscial Research Communications* 191(1): 232–239.

Fabian, Heinz et al. (1994) "Synthetic Post Translationally Modified Human Aβ Peptide Exhibits a Markedly Increased Tendency to Form β–Pleated Sheets in vitro" *Eur. J. Biochem.* 221: 959–964.

Fraser, Paul E. et al. (1994) "Conformation and Fibrillogenesis of Alzheimer Aβ Peptides with Selected Substitution of Charged Residues" *J. Mol. Biol.* 244: 64–73.

Fraser, Paul E. et al. (1992) "Fibril Formation by Primate, Rodent, and Dutch–Hemorrhagic Annalogues of Alzheimer Amyloid β–Protein" *Biochemistry* 32: 10716–10723.

Gorevic, PD et al. (1987) "Ten to Fourteen Residue Peptides of Alzheimer's Disease Protein are Sufficient for Amyloid Fibril Formation and Its Characteristic Xray Diffraction Pattern" *Biochemical and Biophysical Research Communications* 147(2): 854–862.

Gowing, Eric et al. (1994) "Chemical Characterization of Aβ 17–42 Peptide, a Component of Diffuse Amyloid Deposits of Alzheimer Disease" *J. Biol. Chem.* 269(15): 10987–10990.

Halverson, Kurt et al. (1990) "Molecular Determinants of Amyloid Deposition in Alzheimer's Disease: Conformational Studies of Synthetic β–Protein Fragments" *Biochemistry* 29(11): 2639–2644.

Hansen, Morten B. et al. (1989) "Re–examination and Further Developement of a Precise and Rapid Dye Method for Measuring Cell Growth/Cell Kill" *J. Immunol. Meth.* 119: 203–210.

Hardy, John A. and Gerald A. Higgins (1992) "Alzheimer's Disease: The Amyloid Cascade Hypothesis" *Science* 256: 184–185.

Hilbich, Caroline et al. (1991) "Aggregation and Secondary Structure of Synthetic Amyloid βA4 Peptides of Alzheimer's Disease" *J. Mol. Biol.* 218: 149–163.

Hilbich, Caroline et al. (1991) "Human and Rodent Sequence Analogs of Alzheimer's Amyloid β A4 Share Similar Properties and Can Be Solubilized in Buffers of pH 7.4" *Eur. J. Biochem.* 201: 61–69.

Hilibich, Caroline et al. (1992) "Substitutions of Hydrophobic Amino Acids Reduce the Amyloidogencity of Alzheimer's Disease βA4 Peptides" *J. Mol. Biol.* 228: 460–473.

Jarrett, Joseph T. and Peter T. Lansbury, Jr. (1993) "Seeding 'One–Dimensional Crystallization' of Amyloid: A Pathogenic Mechanism in Alzheimer's Disease and Scrapie?" *Cell* 73: 1055–1058.

Jarrett, Joseph T. et al. (1993) "The Carboxy Terminus of the β Amyloid Protein Is Critical for the Seeding of Amyloid Formation: Implications for the Pathogenesis of Alzheimer's Disease" *Biochemistry* 32(18): 4639–4697.

Jarrett, Joseph T. et al. (1994) "Models of the β Protein C–Terminus: Differences in Amyloid Structure May Lead to Segregation of 'Long and Short' Fibrils" *Journal of the American Chemical Society* 116(21): 9741–9742.

Kelly, Jeffery W. and Peter T. Lansbury, Jr. (1994) "A Chemical Approach to Elucidate the Mechanism of Transthyretin and β–Protein Amyloid Fibril Formation" *Int. J. Exp. Clin. Invest* 1: 186–205.

Kirschner, Daniel A. et al. (1987) "Synthetic Peptide Homologous to β Protein from Alzheimer Disease forms Amyloid–like Fibrils in vitro" *Proc. Natl. Acad. Sci. USA* 84: 6953–6957.

Klunk, William E. and Jay W. Pettegrew (1990) "Alzheimer's β–Amyloid Protein Is Covalently Modified When Dissolved in Formic Acid" *Journal of Neurochemistry* 54(6): 2050–2054.

Lansbury, Jr. Peter T. (1992) "In Pursuit of the Molecular Structure of Amyloid Plaque: New Technology Provides Unexpected and Critical Information" *Biochemistry* 31(30): 6866–6870.

LeVine, III Harry (1993) "Thioflavine T Interaction with Synthetic Alzheimer's Disease β–Amyloid Peptides: Detection of Amyloid Aggregation in Solution" *Protein Science* 2: 404–410.

Maggio, John E. et al. (1992) "Reversible in vitro Growth of Alzheimer Disease β—Amyloid Plaques by Deposition of Labeled Amyloid Peptide" *Proc. Natl. Acad. Sci. USA* 89: 5462–5466.

Miller, Brian T. et al. (1994) "Identification and Characterization of O–Biotinylated Hydroxy Amino Acid Residues in Peptides" *Analytical Biochemistry* 219: 240–248.

Orlando, Ron et al. (1992) "Covalent Modification of Alzheimer's Amyloid β—Peptide in Formic Acid Solutions" *Biochemical and Biophysical Research Communications* 184(2): 686–691.

Pike, Christian J. et al. (1993) "Neurodegeneration Induced by β–Amyloid Peptides in vitro: The Role of Peptide Assembly State" *Journal of Neuroscience* 13(4): 1676–1687.

Pike, Christian J. et al. (1995) "Structure—Activity Analyses of β–Amyloid Peptides: Contributions of the β25–35 Region to Aggregation and Neurotoxicity" *Journal of Neurochemistry* 64(1): 253–265.

Schwarzman, Alexander L. et al. (1994) "Transthyretin Sequesters Amyloid β Protein and Prevents Amyloid Formation" *Proc. Natl. Acad. Sci. USA* 8368–8372.

Shearman, Mark S. et al. (1994) "Inhibition of PC12 Cell Redox Activity is a Specific, Early Indicator of the Mechanism of β–Amyloid–Mediated Cell Death" *Proc. Natl. Acad. Sci. USA* 91:1470–1474.

Shen, Chih–Lung et al. (1994) "Effect of Acid Predissolution on Fibril Size and Fibril Flexibility of Synthetic β–Amyloid Peptide" *Biophysical Journal* 67: 1238–1246.

Shen, Chih–Lung et al. (1993) "Light Scattering Analysis of Fibril Growth from the Amino–Terminal Fragment β(1–28) of β–Amyloid Peptide" *Biophysical Journal* 65: 2383–2395.

Snyder, Seth W. et al. (1994) "Amyloid–β Aggregation: Selective Inhibition of Aggregation in Mixtures of Amyloid with Different Chain Lengths" *Biophysical Journal* 67: 1216–1288.

Soreghan, Brian et al. (1994) "Surfactant Properties of Alzheimer's Aβ Peptides and the Mechanism of Amyloid Aggregation" *The Journal of Biological Chemistry* 269(46): 28551–28554.

Sorimachi, Kay and David J. Craik (1994) "Structure Determination of Extracellular Fragments of Amyloid Proteins Involved in Alzheimer's Disease and Dutch–type Hereditary Cerebral Haemorrhage with Amyloidosis" *Eur. J. Biochem* 219: 237–251.

Strittmatter, Warren J. et al. (1993) "Binding of Human Apolipoprotein E to Synthetic Amyloid β Peptide: Isoform–Specific Effects and Implications for Late–Onset Alzheimer Disease" *Proc. Natl. Acad. Sci. USA* 90: 8098–8102.

Tomiyama, Takami et al. (1994) "Racemization of Asp$^{23}$ Residue Affects the Aggregation Properties of Alzheimer Amyloid β Protein Analogues" *J. Biol. Chem.* 269(14): 10205–10208.

Tomski, Sharon J. and Regina M. Murphy (1992) "Kinetics of Aggregation of Synthetic β–Amyloid Peptide" *Archives of Biochemistry and Biophysics* 294(2): 630–638.

Vitek, Michael P. et al. (1994) "Advanced Glycation End Products Contribute to Amyloidosis in Alzheimer Disease" *Proc. Natl. Acad. Sci. USA* 91: 4766–4770.

Weinreb, Paul H. et al. (1994) "Peptide Models of a Hydrophobic Cluster at the C–Terminus of the β–Amyloid Protein" *Journal of the American Chemical Society* 116(23): 10835–10836.

Flood, J.F. et al., (1994) "Topography of a Binding Site for Small Amnestic Peptides Deduced from Structure–Activity Studies: Relation to Amnestic Effect of Amyloid βProtein," *Proc. Natl. Acad. Sci. USA* vol. 91, pp. 380–384.

Inouye, H. et al. (1993) "Structure of Beta–Crystallite Assemblies Formed by Alzheimer β–Amyloid Protein Analogs: Analysis by X–ray Diffraction," *Chemical Abstracts* vol. 119, p. 349, Abstract No. 119; 23024a.

Sonnenberg–Reines, J. et al. (1993) "Biotinylated and Cysteine Modified Peptides as Useful Reagents for Studying the Inhibition of Putative N–terminal B–Amyloid Peptide Enzymes," *Society for Neuroscience Abstracts* vol. 19 (1–3), p. 861.

Vyas, S. B. et al. "Characterization of Aggregation in Alzheimer β–protein Using Synthetic Peptide Fragments on Reverse–Phase Matrix," in *Peptides, Chemistry and Biology* (J.A. Smith and J.E. Rivier, eds.), ESCOM Leiden, 1992, pp. 278–279.

Woods, S.J. et al. (1995) "Prolines and Amyloidogenicity in Fragments of the Alzheimer's Peptide β/A4, " *Biochemistry* vol. 34, 724–730.

Koudinov et al, The Soluble Form of Alzheimers . . . Biochem. Biophys. Res. Comm. vol. 205, No. 2, pp. 1164–1171, Dec. 15, 1994.

Dayhoff, Atlas of Protein Sequence and Structure, vol. 5, Published 1972 by Nat. Biomed. Res. Found. p. 96.

Lab. Invest., vol. 56, No. 5, Issued 1987, Niewold et al, "Enhancement of Amyloid Induction by Amyloid . . . ", pp. 544–549.

Hendrix et al, A Convergent Synthesis of the Amyloid Protein of Alzheimer's Disease, J. Am Chem. Soc. 1992, vol. 114, pp. 7930–7931.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

```
Asp  Ala  Glu  Phe  Arg  His  Asp  Ser  Gly  Tyr  Glu  Val  His  His  Gln  Lys
1                   5                        10                           15

Leu  Val  Phe  Phe  Ala  Glu  Asp  Val  Gly  Ser  Asn  Lys  Gly  Ala  Ile  Ile
              20                       25                        30

Gly  Leu  Met  Val  Gly  Gly  Val  Val  Ile  Ala  Thr
              35                      40
```

( 2 ) INFORMATION FOR SEQ ID NO:2:

( i ) SEQUENCE CHARACTERISTICS:
        ( A ) LENGTH: 103 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

```
Glu  Val  Lys  Met  Asp  Ala  Glu  Phe  Arg  His  Asp  Ser  Gly  Tyr  Glu  Val
1                   5                        10                           15

His  His  Gln  Lys  Leu  Val  Phe  Phe  Ala  Glu  Asp  Val  Gly  Ser  Asn  Lys
              20                       25                        30

Gly  Ala  Ile  Ile  Gly  Leu  Met  Val  Gly  Gly  Val  Val  Ile  Ala  Thr  Val
              35                      40                        45

Ile  Val  Ile  Thr  Leu  Val  Met  Leu  Lys  Lys  Lys  Gln  Tyr  Thr  Ser  Ile
         50                      55                       60

His  His  Gly  Val  Val  Glu  Val  Asp  Ala  Ala  Val  Thr  Pro  Glu  Glu  Arg
65                            70                       75                      80
```

-continued

```
His Leu Ser Lys Met Gln Gln Asn Gly Tyr Glu Asn Pro Thr Tyr Lys
              85                      90                      95

Phe Phe Glu Gln Met Gln Asn
                100
```

( 2 ) INFORMATION FOR SEQ ID NO:3:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY:
        ( B ) LOCATION:
        ( D ) OTHER INFORMATION: /note= "Xaa"is a hydrophobic amino
            acid."

( x i ) SEQUENCE DESCRIPTION: SEQ ID NO:3:

```
Asp Ala Glu Phe Arg His Asp Ser Gly Tyr Glu Val His His Gln Lys
1                   5                   10                  15

Leu Val Xaa Xaa Ala Glu Asp Val Gly Ser Asn Lys Gly Ala Ile Ile
            20                  25                  30

Gly Leu Met Val Gly Gly Val Val Ile Ala Thr
            35                  40
```

MODULATORS OF BETA-AMYLOID PEPTIDE AGGREGATION

BACKGROUND OF THE INVENTION

Alzheimer's disease (AD), first described by the Bavarian psychiatrist Alois Alzheimer in 1907, is a progressive neurological disorder that begins with short term memory loss and proceeds to disorientation, impairment of judgement and reasoning and, ultimately, dementia. The course of the disease usually leads to death in a severely debilitated, immobile state between four and 12 years after onset. AD has been estimated to afflict 5 to 11 percent of the population over age 65 and as much as 47 percent of the population over age 85. The societal cost for managing AD is upwards of 80 billion dollars annually, primarily due to the extensive custodial care required for AD patients. Moreover, as adults born during the population boom of the 1940's and 1950's approach the age when AD becomes more prevalent, the control and treatment of AD will become an even more significant health care problem. Currently, there is no treatment that significantly retards the progression of the disease. For reviews on AD, see Selkoe, D. J. *Sci. Amer.*, November 1991, pp. 68–78; and Yankner, B. A. et al. (1991) *N. Eng. J Med.* 325:1849–1857.

It has recently been reported (Games et al. (1995) *Nature* 373:523–527) that an Alzheimer-type neuropathology has been created in transgenic mice. The transgenic mice express high levels of human mutant amyloid precursor protein and progressively develop many of the pathological conditions associated with AD.

Pathologically, AD is characterized by the presence of distinctive lesions in the victim's brain. These brain lesions include abnormal intracellular filaments called neurofibrillary tangles (NTFs) and extracellular deposits of amyloidogenic proteins in senile, or amyloid, plaques. Amyloid deposits are also present in the walls of cerebral blood vessels of AD patients. The major protein constituent of amyloid plaques has been identified as a 4 kilodalton peptide called β-amyloid peptide (β-AP)(Glenner, G. G. and Wong, C. W. (1984) *Biochem. Biophys. Res. Commun.* 120:885–890; Masters, C. et al. (1985) *Proc. Natl Acad. Sci. USA* 82:4245–4249). Diffuse deposits of β-AP are frequently observed in normal adult brains, whereas AD brain tissue is characterized by more compacted, dense-core β-amyloid plaques. (See e.g., Davies, L. et al. (1988) *Neurology* 38:1688–1693) These observations suggest that β-AP deposition precedes, and contributes to, the destruction of neurons that occurs in AD. In further support of a direct pathogenic role for β-AP, β-amyloid has been shown to be toxic to mature neurons, both in culture and in vivo. Yankner, B. A. et al. (1989) *Science* 245:417–420; Yankner, B. A. et al. (1990) *Proc. Natl. Acad. Sci. USA* 87:9020–9023; Roher, A. E. et al. (1991) *Biochem. Biophys. Res. Commun.* 174:572–579; Kowall, N. W. et al. (1991) *Proc. Natl. Acad. Sci. USA* 88:7247–7251. Furthermore, patients with hereditary cerebral hemorrhage with amyloidosis-Dutch-type (HCHWA-D), which is characterized by diffuse β-amyloid deposits within the cerebral cortex and cerebrovasculature, have been shown to have a point mutation that leads to an amino acid substitution within β-AP. Levy, E. et al. (1990) *Science* 248:1124–1126. This observation demonstrates that a specific alteration of the β-AP sequence can cause β-amyloid to be deposited.

Natural β-AP is derived by proteolysis from a much larger protein called the amyloid precursor protein (APP). Kang, J. et al. (1987) *Nature* 325:733; Goldgaber, D. et al. (1987) *Science* 235:877; Robakis, N. K. et al. (1987) *Proc. Natl. Acad. Sci. USA* 84:4190; Tanzi, R. E. et al. (1987) *Science* 235:880. The APP gene maps to chromosome 21, thereby providing an explanation for the β-amyloid deposition seen at an early age in individuals with Down's syndrome, which is caused by trisomy of chromosome 21. Mann, D. M. et al. (1989) *Neuropathol. AppL. Neurobiol.* 15:317; Rumble, B. et al. (1989) *N. Eng J. Med.* 320:1446. APP contains a single membrane spanning domain, with a long amino terminal region (about two-thirds of the protein) extending into the extracellular environment and a shorter carboxy-terminal region projecting into the cytoplasm. Differential splicing of the APP messenger RNA leads to at least five forms of APP, composed of either 563 amino acids (APP-563), 695 amino acids (APP-695), 714 amino acids (APP-714), 751 amino acids (APP-751) or 770 amino acids (APP-770).

Within APP, naturally-occurring β amyloid peptide begins at an aspartic acid residue at amino acid position 672 of APP-770. Naturally-occurring β-AP derived from proteolysis of APP is 39 to 43 amino acid residues in length, depending on the carboxy-terminal end point, which exhibits heterogeneity. The predominant circulating form of β-AP in the blood and cerebrospinal fluid of both AD patients and normal adults is β1–40 ("short β"). Seubert, P. et al. (1992) *Nature* 359:325; Shoji, M. et al. (1992) *Science* 258:126. However, β1–42 and β1–43 ("long β") also are forms in β-amyloid plaques. Masters, C. et al. (1985) *Proc. Natl. Acad. Sci. USA* 82:4245; Miller, D. et al. (1993) *Arch. Biochem. Biophys.* 301:41; Mori, H. et al. (1992) *J. Biol. Chem.* 267:17082. Although the precise molecular mechanism leading to β-APP aggregation and deposition is unknown, the process has been likened to that of nucleation-dependent polymerizations, such as protein crystallization, microtubule formation and actin polymerization. See e.g., Jarrett, J. T. and Lansbury, P. T. (1993) *Cell* 73:1055–1058. In such processes, polymerization of monomer components does not occur until nucleus formation. Thus, these processes are characterized by a lag time before aggregation occurs, followed by rapid polymerization after nucleation. Nucleation can be accelerated by the addition of a "seed" or preformed nucleus, which results in rapid polymerization. The long β forms of β-AP have been shown to act as seeds, thereby accelerating polymerization of both long and short β-AP forms. Jarrett, J. T. et al. (1993) *Biochemistry* 32:4693.

In one study, in which amino acid substitutions were made in β-AP, two mutant β peptides were reported to interfere with polymerization of non-mutated β-AP when the mutant and non-mutant forms of peptide were mixed. Hilbich, C. et al. (1992) *J. Mol. Biol.* 228:460–473. However, equimolar amounts of the mutant and non-mutant (i.e., natural) β amyloid peptides were used to see this effect and the mutant peptides were reported to be unsuitable for use in vivo. Hilbich, C. et al. (1992), *supra.*

SUMMARY OF THE INVENTION

The present invention provides β amyloid modulators that affect the aggregation of natural β-amyloid and therefore can be used to treat subjects having a disorder associated with β-amyloidosis, e.g. Alzheimer's disease (AD). The aggregation and deposition of β-amyloid play an important role in the pathology of AD. The modulators of the present invention can affect aggregation of natural β amyloid peptides when present at a lower concentration than that of the natural β amyloid peptides and further are suitable for therapeutic use in vivo.

This invention generally pertains to compounds that are capable of altering the aggregation of natural β amyloid peptides (β-AP) when the compounds of the invention are contacted with the natural β-AP. These compounds, referred to as β amyloid modulators, either can promote β-AP aggregation or, more preferably, can inhibit β-AP aggregation. Moreover, the preferred modulators of the invention are capable of altering natural β-AP aggregation even when the natural β-AP concentration is in molar excess compared to the concentration of the modulator. Thus, a small amount of a modulator of the invention acts to disrupt the natural β amyloid aggregation process or rate. Because of their ability to alter, and preferably inhibit, natural β-AP aggregation, the modulators of the invention are useful therapeutically in the treatment of disorders associated with β amyloidosis, in particular Alzheimer's disease. Moreover, the modulators of the invention can be used diagnostically in assays to detect and quantitate natural β-AP in an in vitro sample, such as a sample of biological fluid.

In one embodiment, a modulator of the invention is a β-amyloid peptide compound comprising a formula:

wherein Xaa is a β-amyloid peptide, A is a modulating group attached directly or indirectly to the β-amyloid peptide of the compound such that the compound inhibits aggregation of natural β-amyloid peptides when contacted with the natural β-amyloid peptides, and n is an integer selected such that the compound inhibits aggregation of natural β-amyloid peptides when contacted with the natural β-amyloid peptides.

Preferably, the β-amyloid peptide of the compound has an amino-terminal amino acid residue corresponding to position 668 of β-amyloid precursor protein-770 (APP-770), or to a residue carboxy-terminal to position 668. Even more preferably, the β-amyloid peptide of the compound has an amino-terminal amino acid residue corresponding to position 672 of APP-770, or to a residue carboxy-terminal to position 672. Preferably, the β-amyloid peptide of the compound has between 6 and 60 amino acid residues, more preferably between 10 and 43 amino acid residues, and even more preferably between 10 and 25 amino acid residues. A preferred β-amyloid peptide of the compound consists of an amino acid sequence shown in SEQ ID NO: 2, or an amino-terminal or carboxy-terminal deletion thereof having at least 6 amino acid residues.

A modulating group(s) ("A") can be attached to the β-amyloid peptide of the compound through, for example, the amino terminus of the peptide, the carboxy-terminus of the peptide or the side chain(s) of one or more amino acid residues. The number of modulating groups ("n") attached to the peptide is selected such that the β-amyloid peptide is capable of performing its intended function of modulating aggregation of natural β-amyloid peptides. The number of modulating groups is preferably between 1 and 60, more preferably between 1 and 30 and even more preferably between 1 and 10 or 1 and 5. A preferred modulating group, in particular for modifying the amino terminus of the β amyloid peptide of the compound, is a biotin compound.

In another embodiment, the invention provides a modulator of β-amyloid aggregation which alters aggregation of natural β-amyloid peptides when contacted with a molar excess amount of natural β-amyloid peptides. The modulator may promote or inhibit aggregation of natural β-amyloid peptides, and preferably alters β-AP aggregation of at least a 10-fold molar excess amount of natural β-AP. More preferably, the modulator alters aggregation of at least a 100-fold molar excess amount of natural β-AP.

Methods for selecting a modulator of β-amyloid aggregation of the invention are also provided. In a preferred embodiment, the method involves contacting a test compound with an molar excess amount of natural β-amyloid peptides (β-AP), measuring the aggregation of the natural β-AP in the presence of the test compound and selecting a test compound that reduces the aggregation of the natural β-AP, compared to the aggregation of the natural β-AP in the absence of the test compound. Aggregation of the natural β-AP can be measured, for example, by measuring turbidity of a solution of the natural β-AP in the presence of the test compound.

Another aspect of the invention pertains to a pharmaceutical composition comprising a modulator of the invention in a therapeutically effective amount sufficient to alter, and preferably inhibit, aggregation of natural β-amyloid peptides, and a pharmaceutically acceptable carrier. The pharmaceutically acceptable carrier can be suitable for parenteral administration. The carrier also can be suitable for intrathecal administration (e.g., intraspinal or intracerebral administration). The pharmaceutical composition of the invention can be provided as a packaged formulation including, for example, the composition in a container and instructions for administration of the composition.

Yet another aspect of the invention pertains to a method for altering, and preferably inhibiting, aggregation of natural β-amyloid peptides. The method involves contacting the natural β-amyloid peptides with a modulator of the invention such that aggregation of the natural β-amyloid peptides is altered, and preferably inhibited. In one embodiment of the method, the modulator is contacted with a molar excess amount of natural β-AP. The method of the invention can be used to detect and quantitate natural β-AP in vitro (e.g., in a biological sample). Furthermore, a modulator can be contacted with natural β-AP in a subject (e.g., in the brain parenchyma or cerebrospinal fluid of the subject) by administering the modulator to the subject to thereby alter, and preferably inhibit, natural β-AP aggregation in the subject. The modulator preferably is administered directly into the central nervous system (CNS) of the subject. For example, the modulator may be administered into the CNS through a catheter (e.g., intraspinally), via a surgically implanted infusion pump, through a reservoir (e.g., intracerebrally) or by direct injection; (e.g., lumbar puncture). Accordingly, medical devices such as syringes, pumps, reservoirs, catheters and the like containing a pharmaceutical composition of the invention are also encompassed by the invention.

DETAILED DESCRIPTION OF THE INVENTION

Figure 1:
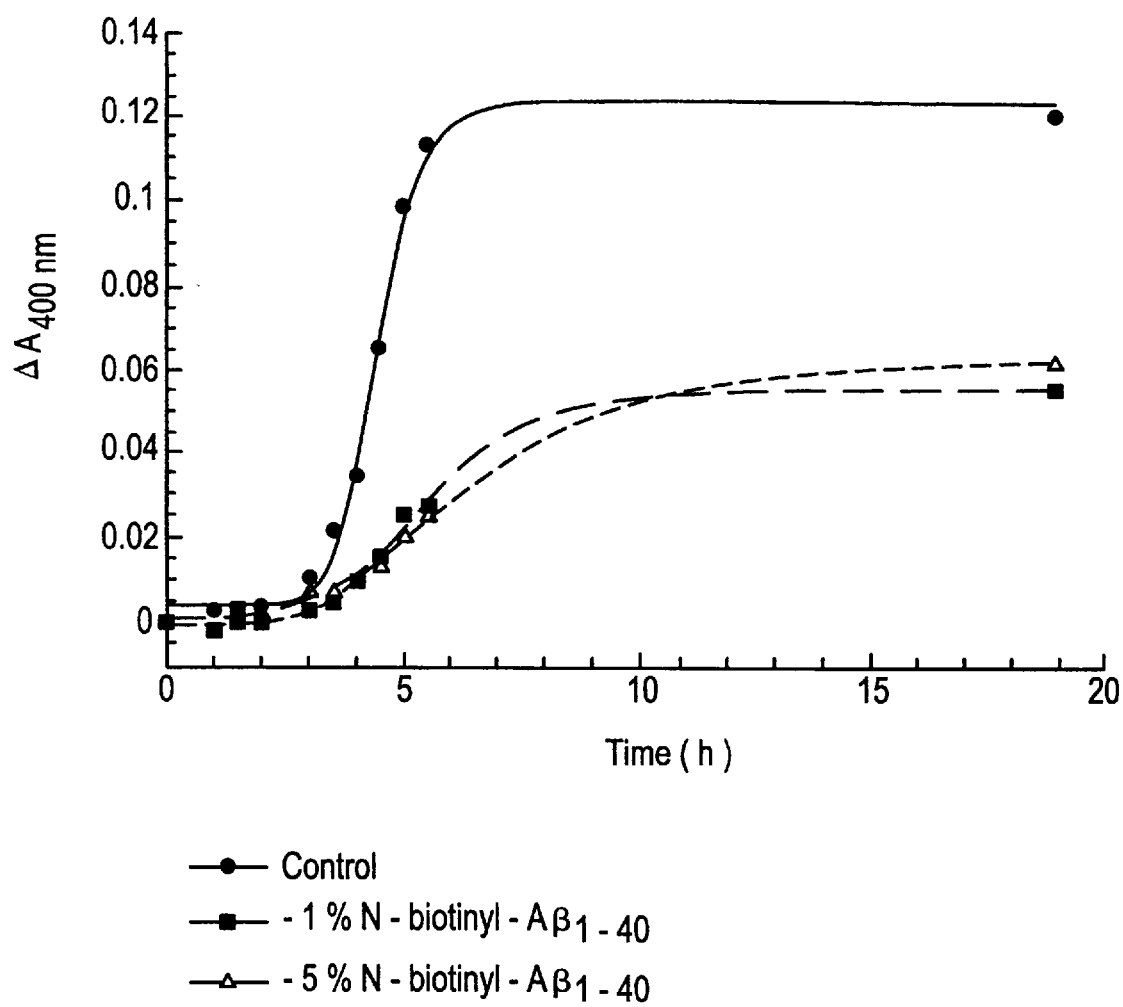
FIG. 1 is a graphic representation of the turbidity of a β-AP$_{1-40}$ solution, as measured by optical density at 400 nm, either in the absence of a β-amyloid modulator or in the presence of the β-amyloid modulator N-biotinyl-βAP$_{1-40}$ (1 %, or 5%).

This invention pertains to compounds, and pharmaceutical compositions thereof, that can modulate the aggregation of natural β amyloid peptides (β-AP). A compound of the invention, referred to herein interchangeably as a β amyloid peptide modulator, a β amyloid modulator or simply a modulator, alters the aggregation of natural β-AP when the modulator is contacted with natural β-AP. Thus, a compound of the invention acts to alter the natural aggregation process or rate for β-AP, thereby disrupting this process.

Accordingly, as used herein, a "modulator" of β-amyloid aggregation is intended to refer to an agent that, when contacted with natural β amyloid peptides, alters the aggregation of the natural β amyloid peptides. The term "aggregation of β amyloid peptides" refers to a process whereby the peptides associate with each other to form a multimeric, largely insoluble complex. The term "aggregation" further is intended to encompass β amyloid fibril formation and also encompasses β-amyloid plaques.

The terms "natural β-amyloid peptide" and "natural β-AP", used interchangeably herein, are intended to encompass naturally occurring proteolytic cleavage products of the β amyloid precursor protein (APP), including β amyloid peptides having 39–43 amino acids (i.e., β1–39, β1–40, β1–41, β1–42 and β1–43). The amino-terminal amino acid residue of natural β-AP corresponds to the aspartic acid residue at position 672 of the 770 amino acid residue form of APP ("APP-770"). The 43 amino acid long form of natural β-AP has the amino acid sequence:

DAEFRHDSGYEVHHQKLVFFAEDVGSNK-
GAIIGLMVGGVVIAT (SEQ ID NO: 1), whereas the shorter forms have 1–4 amino acid residues deleted from the carboxy-terminal end.

In the presence of a modulator of the invention, aggregation of natural β amyloid peptides is "altered". The various forms of the term "alteration" are intended to encompass both inhibition of β-AP aggregation and promotion of β-AP aggregation. Aggregation of natural β-AP is "inhibited" in the presence of the modulator when there is a decrease in the amount and/or rate of β-AP aggregation as compared to the amount and/or rate of β-AP aggregation in the absence of the modulator. The various forms of the term "inhibition" are intended to include both complete and partial inhibition of β-AP aggregation. Preferably, aggregation is inhibited at least 10%, more preferably, at least 20%, 30%, 40% or 50%. Alternatively, the various forms of the term "promotion" refer to an increase in the amount and/or rate of β-AP aggregation in the presence of the modulator, as compared to the amount and/or rate of β-AP aggregation in the absence of the modulator.

In a preferred embodiment, the modulators of the invention are capable of altering β-AP aggregation when contacted with a molar excess amount of natural β-AP. A "molar excess amount of natural β-AP" refers to a concentration of natural β-AP, in moles, that is greater than the concentration, in moles, of the modulator. For example, if the modulator and β-AP are both present at a concentration of 1 μM, they are said to be "equimolar", whereas if the modulator is present at a concentration of 1 μM and the β-AP is present at a concentration of 5 μM, the β-AP is said to be present at a 5-fold molar excess amount compared to the modulator. Preferably, a modulator of the invention is effective at altering natural β-AP aggregation when the natural β-AP is present at at least a 5-fold, and more preferably at least a 10-fold, 20-fold, 50-fold, 100-fold, 500-fold or 1000-fold molar excess compared to the concentration of the modulator.

In one embodiment, a modulator of the invention is a β-amyloid peptide compound comprising the formula:

wherein Xaa is a β-amyloid peptide, A is a modulating group attached directly or indirectly to the β-amyloid peptide of the compound such that the compound inhibits aggregation of natural β-amyloid peptides when contacted with the natural β-amyloid peptides, and n is an integer selected such that the compound inhibits aggregation of natural β-amyloid peptides when contacted with the natural β-amyloid peptides.

Preferably, β-amyloid peptide of the compound has an amino-terminal amino acid residue corresponding to position 668 of β-amyloid precursor protein-770 (APP-770) or to a residue carboxy-terminal to position 668 of APP-770. The amino acid sequence of APP-770 from position 668 to position 770 (i.e., the carboxy terminus) is shown below and in SEQ ID NO:2:

EVKMDAEFRHDSGYEVHHQKLVFFAED-
VGSNKGAIIGLMVGGVVIATVIVITL VMLKKKQYTSIHH-
GVVEVDAAVTPEERHLSKMQQNGYENPTYKFFEQMQN.

More preferably, the amino-terminal amino acid residue of the β-amyloid peptide corresponds to position 672 of APP-770 (position 5 of the amino acid sequence of SEQ ID NO: 2) or to a residue carboxy-terminal to position 672 of APP-770. Although the β-amyloid peptide of the compound may encompass the 103 amino acid residues corresponding to positions 668–770 of APP-770, preferably the peptide is between 6 and 60 amino acids in length, more preferably between 10 and 43 amino acids in length and even more preferably between 10 and 25 amino acid residues in length.

As used herein, the term "β amyloid peptide", as used in a modulator of the invention is intended to encompass peptides having an amino acid sequence identical to that of the natural sequence in APP, as well as peptides having acceptable amino acid substitutions from the natural sequence. Acceptable amino acid substitutions are those that do not affect the ability of the peptide to alter natural β-AP aggregation. Moreover, particular amino acid substitutions may further contribute to the ability of the peptide to alter natural β-AP aggregation and/or may confer additional beneficial properties on the peptide (e.g., increased solubility, reduced associated with other amyloid proteins, etc). For example, substitution of hydrophobic amino acid residues for the two phenylalanine residues at positions 19 and 20 of natural β-AP (positions 19 and 20 of the amino acid sequence shown in SEQ ID NO: 1) may further contribute to the ability of the peptide to alter β-AP aggregation (see Hilbich, C. (1992) *J. Mol. Biol.* 228:460–473). Thus, in one embodiment, the β-AP of the compound consists of the amino acid sequence shown below and in SEQ ID NO: 3:

DAEFRHDSGYEVHHQKLV(Xaa$_{19}$)(Xaa$_{20}$)AEDVGSNKGAIIG
LMVGGVVIAT (or an amino-terminal or carboxy-terminal deletion thereof), wherein Xaa is a hydrophobic amino acid. Examples of hydrophobic amino acids are isoleucine, leucine, threonine, serine, alanine, valine or glycine. Preferably, $F_{19}F_{20}$ is substituted with $T_{19}T_{20}$ or $G_{19}I_{20}$.

Other suitable amino acid substitutions include replacement of amino acids in the human peptide with the corresponding amino acids of the rodent β-AP peptide. The three amino acid residues that differ between human and rat β-AP are at positions 5, 10 and 13 of the amino acid sequence shown in SEQ ID NOs: 1 and 3. A human β-AP having the human to rodent substitutions Arg$_5$ to Gly, Tyr$_{10}$ to Phe and His$_{13}$ to Arg has been shown to retain the properties of the human peptide (see Fraser, P. E. et al. (1992) *Biochemistry* 31:10716–10723; and Hilbich, C. et al. (1991) *Eur. J Biochem.* 201:61–69). Accordingly, a human β-AP having rodent β-AP a.a. substitutions is suitable for use in a modulator of the invention.

Other possible β-AP amino acid substitutions are described in Hilbich, C. et al. (1991) *J Mol. Biol.* 218:149–163; and Hilbich, C. (1992) *J Mol. Biol.* 228:460–473. Moreover, amino acid substitutions that affect the ability of β-AP to associate with other proteins can be introduced. For example, one or more amino acid substitutions that reduce the ability of β-AP to associate with the serpin enzyme complex (SEC) receptor, α1-antichymotrypsin (ACT) and/or apolipoprotein E (ApoE) can be introduced. A preferred substitution for reducing binding to the SEC receptor is $L_{34}M_{35}$ to $A_{34}A_{35}$ (at positions 34 and 35 of the amino acid sequences shown in SEQ ID NOs: 1 and 3). A preferred substitution for reducing binding to ACT is $S_8$ to $A_8$ (at position 8 of the amino acid sequences shown in SEQ ID NOs: 1 and 3).

Alternative to β-AP amino acid substitutions described herein or known in the art, a modulator composed, at least in part, of an amino acid-substituted β amyloid peptide can be prepared by standard techniques and tested for the ability to alter β-AP aggregation using an aggregation assay described herein. To retain the properties of the original modulator, preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Accordingly, a modulator composed of a β amyloid peptide having an amino acid sequence that is mutated from that of the wild-type sequence in APP-770 yet which still retains the ability to alter natural β-AP aggregation is within the scope of the invention.

As used herein, the term "β amyloid peptide" is further intended to include peptide analogues or peptide derivatives or peptidomimetics that retain the ability to alter natural β-AP aggregation as described herein. For example, a β amyloid peptide of a modulator of the invention may be modified to increase its stability, bioavailability, solubility, etc. The terms "peptide analogue", "peptide derivative" and "peptidomimetic" as used herein are intended to include molecules which mimic the chemical structure of a peptide and retain the functional properties of the peptide. Approaches to designing peptide analogs are known in the art. For example, see Farmer, P. S. in *Drug Design* (E.J. Ariens, ed.) Academic Press, New York, 1980, vol. 10, pp. 119–143; Ball. J. B. and Alewood, P. F. (1990) *J Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. Examples of peptide analogues, derivatives and peptidomimetics include peptides substituted with one or more benzodiazepine molecules (see e.g., James, G. L. et al. (1993) *Science* 260:1937–1942), peptides with methylated amide linkages and "retro-inverso" peptides (see U.S. Pat. No. 4,522,752 by Sisto).

In a modulator of the invention having the formula shown above, a modulating group ("A") is attached directly or indirectly to the β-amyloid peptide of the modulator. For example, the modulating group can be directly attached by covalent coupling to the β-amyloid peptide or the modulating group can be attached indirectly by a stable non-covalent association. In one embodiment of the invention, the modulating group is attached to the amino-terminus of the β-amyloid peptide of the modulator. Accordingly, the modulator can comprise a compound having a formula:

$$A-\overset{H}{N}-(Xaa).$$

Alternatively, in another embodiment of the invention, the modulating group is attached to the carboxy-terminus of the β-amyloid peptide of the modulator. Accordingly, the modulator can comprise a compound having a formula:

$$(Xaa)-\overset{O}{\underset{\|}{C}}-A.$$

In yet another embodiment, the modulating group is attached to the side chain of at least one amino acid residue of the β-amyloid peptide of the compound (e.g., through the epsilon amino group of a lysyl residue(s), through the carboxyl group of an aspartic acid residue(s) or a glutamic acid residue(s), through a hydroxy group of a tyrosyl residue (s), a serine residue(s) or a threonine residue(s) or other suitable reactive group on an amino acid side chain).

The modulating group is selected such that the compound inhibits aggregation of natural β-amyloid peptides when contacted with the natural β-amyloid peptides. Accordingly, since the β-AP peptide of the compound is modified from its natural state, the modulating group "A" as used herein is not intended to include hydrogen. In a preferred embodiment, the modulating group is a biotin compound of the formula:

$$\begin{array}{c} W \\ \diagdown \\ X_2 \\ \diagdown \\ X_3 \underline{\qquad} R_1 - \overset{O}{\underset{\|}{C}} - Y \end{array}$$

wherein $X_1$–$X_3$ are each independently selected from the group consisting of S, O and $NR_1$, wherein $R_1$ is hydrogen, or an aryl, lower alkyl, alkenyl or alkynyl moiety; W is =O or $N(R_1)_{2m}$; $R_1$ is a lower alkylenyl moiety and Y is a direct bond or a spacer molecule selected for its ability to react with a target group on a β-AP. At least one of $X_1$–$X_3$ or W is an $N(R_1)_2$ group.

The term "aryl" is intended to include aromatic moieties containing substituted or unsubstituted ring(s), e.g., benzyl, napthyl, etc. Other more complex fused ring moieties also are intended to be included.

The term "lower alkyl or alkylenyl moiety" refers to a saturated, straight or branched chain (or combination thereof) hydrocarbon containing 1 to about 6 carbon atoms, more preferably from 1 to 3 carbon atoms. The terms "lower alkenyl moiety" and "lower alkynyl moiety" refer to unsaturated hydrocarbons containing 1 to about 6 carbon atoms, more preferably 1 to 3 carbon atoms. Preferably, $R_1$ contains 1 to 3 carbon atoms. Preferably, $R_1$ contains 4 carbon atoms.

The spacer molecule (Y) can be, for example, a lower alkyl group or a linker peptide, and is preferably selected for its ability to link with a free amino group (e.g., the α-amino group at the amino-terminus of a β-AP). Thus, in a preferred embodiment, the biotin compound modifies the amino-terminus of a β-amyloid peptide.

Additional suitable modulating groups may include other cyclic and heterocyclic compounds and other compounds having similar steric "bulk". In a modulator of the invention, a single modulating group may be attached to a β-amyloid peptide (e.g., n=1 in the formula shown above) or multiple modulating groups may be attached to the peptide. The number of modulating groups is selected such that the compound inhibits aggregation of natural β-amyloid peptides when contacted with the natural β-amyloid peptides. However, n preferably is an integer between 1 and 60, more preferably between 1 and 30 and even more preferably between 1 and 10 or 1 and 5.

Modulators of the invention can be prepared by standard techniques known in the art. The peptide component of a modulator composed, at least in part of a peptide, can be synthesized using standard techniques such as those described in Bodansky, M. *Principles of Peptide Synthesis*, Springer Verlag, Berlin (1993) and Grant, G. A. (ed.). *Synthetic Peptides: A User's Guide*, W. H. Freeman and Company, New York (1992). Automated peptide synthesizers are commercially available (e.g., Advanced ChemTech Model 396; Milligen/Biosearch 9600). Additionally, one or more modulating groups can be attached to a β-amyloid peptide by standard methods, for example using methods for reaction through an amino group (e.g., the alpha-amino group at the amino-terminus of a peptide or the epsilon amino group of a lysyl residue), a carboxyl group (e.g., at the carboxy terminus of a peptide or on an aspartic or glutamic acid residue), a hydroxyl group (e.g., on a tyrosine, serine or threonine residue) or other suitable reactive group on an amino acid side chain (see e.g., Greene, T. W and Wuts, P. G. M. *Protective Groups in Organic Synthesis*, John Wiley and Sons, Inc., New York (1991). Synthesis of preferred β amyloid modulators is described further in Example 1.

Another aspect of the invention pertains to a method for selecting a modulator of β-amyloid aggregation. In the method, a test compound is contacted with natural β amyloid peptides, the aggregation of the natural β-AP is measured and a modulator is selected based on the ability of the test compound to alter the aggregation of the natural β-AP (e.g., inhibit or promote aggregation). In a preferred embodiment, the test compound is contacted with a molar excess amount of the natural β-AP. The amount and/or rate of natural β-AP aggregation in the presence of the test compound can be determined by a suitable assay indicative of β-AP aggregation, as described herein.

In a preferred assay, the natural β-AP is dissolved in solution in the presence of the test compound and aggregation of the natural β-AP is assessed by the turbidity of the solution over time, as determined by the optical density of the solution (described further in Example 2; see also Jarrett et al. (1993) *Biochemistry* 32:4693–4697). Typically, the absorbance at 400 nm ($A_{400\ nm}$) of the β-AP solution is measured, either in the presence or absence of the test compound. In the absence of a β-amyloid modulator, the $A_{400\ nm}$ of the solution typically stays relatively constant during a lag time in which the β-AP remains in solution, but then the $A_{400\ nm}$ of the solution rapidly increases as the β-AP aggregates and comes out of solution, ultimately reaching a plateau level (i.e., the $A_{400\ nm}$ of the solution exhibits sigmoidal kinetics over time). In contrast, in the presence of a test compound that inhibits β-AP aggregation, the $A_{400\ nm}$ of the solution is reduced compared to when the modulator is absent. Thus, in the presence of the inhibitory modulator, the solution may exhibit an increased lag time, a decreased slope of aggregation and/or a lower plateau level compared to when the modulator is absent. This method for selecting a modulator of β-amyloid polymerization can similarly be used to select modulators that promote β-AP aggregation. Thus, in the presence of a modulator that promotes β-AP aggregation, the $A_{400\ nm}$ of the solution is increased compared to when the modulator is absent (e.g., the solution may exhibit an decreased lag time, increase slope of aggregation and/or a higher plateau level compared to when the modulator is absent).

Other assays suitable for use in the screening method of the invention are described further in Example 2. For example, aggregation can be assayed based on enhanced emission of the dye Thioflavine T when contacted with β-AP or by visualization of high molecular weight β-AP aggregates on SDS-PAGE gels. Moreover, β-AP aggregation can be assessed by electron microscopy (EM) of the β-AP preparation in the presence or absence of the modulator. For example, β amyloid fibril formation, which is detectable by EM, is reduced in the presence of a modulator that inhibits β-AP aggregation (i.e., there is a reduced amount or number of β-fibrils in the presence of the modulator), whereas β fibril formation is increased in the presence of a modulator that promotes β-AP aggregation (i.e., there is an increased amount or number of β-fibrils in the presence of the modulator).

Another aspect of the invention pertains to pharmaceutical compositions of the β-amyloid modulators of the invention. These compositions include a β amyloid modulator in a therapeutically effective amount sufficient to alter, and preferably inhibit, aggregation of natural β-amyloid peptides, and a pharmaceutically acceptable carrier. A "therapeutically effective amount" refers to an amount effective, at dosages and for periods of time necessary, to achieve the desired result. A therapeutically effective amount of modulator may vary according to factors such as the disease state, age, sex, and weight of the individual, and the ability of the modulator to elicit a desired response in the individual. Dosage regimens may be adjusted to provide the optimum therapeutic response. A therapeutically effective amount is also one in which any toxic or detrimental effects of the modulator are outweighed by the therapeutically beneficial effects. The potential neurotoxicity of the modulators of the invention can be assayed as described in Example 3 and a therapeutically effective modulator can be selected which does not exhibit significant neurotoxicity. In a preferred embodiment, a therapeutically effective amount of a modulator is sufficient to alter, and preferably inhibit, aggregation of a molar excess amount of natural β-amyloid peptides.

One factor that may be considered when determining a therapeutically effective amount of a β amyloid modulator is the concentration of natural β-AP in a biological compartment of a subject, such as in the cerebrospinal fluid (CSF) of the subject. The concentration of natural β-AP in the CSF has been estimated at 3 nM (Schwartzman, (1994) *Proc. Natl. Acad. Sci. USA* 91:8368–8372). A non-limiting range for a therapeutically effective amount of a β amyloid modulator is 0.01 nM–10 μM. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

As used herein "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral administration. More preferably, the carrier is suitable for administration into the central nervous system (e.g., intraspinally or intracerebrally). Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, monostearate salts and gelatin. Moreover, the modulators can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

Sterile injectable solutions can be prepared by incorporating the active compound (e.g., β-amyloid modulator) in the required amount in an appropriate solvent with one or a combination of ingredients enumerated above, as required, followed by filtered sterilization. Generally, dispersions arc prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The amount of active compound in the composition may vary according to factors such as the disease state, age, sex, and weight of the individual, each of which may affect the amount of natural β-AP in the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In another embodiment, a pharmaceutical composition of the invention is provided as a packaged formulation. The packaged formulation may include a pharmaceutical composition of the invention in a container and printed instructions for administration of the composition for treating a subject having a disorder associated with β-amyloidosis, e.g. Alzheimer's disease.

Another aspect of the invention pertains to methods for altering aggregation of natural β-amyloid peptides. In the methods of the invention, natural β amyloid peptides are contacted with a β amyloid modulator such that aggregation of the natural β amyloid peptides is altered. In one embodiment, the modulator inhibits aggregation of the natural β amyloid peptides. In another embodiment, the modulator promotes aggregation of the natural β amyloid peptides. Preferably, aggregation of a molar excess amount of β-AP, relative to the amount of modulator, is altered upon contact with the modulator.

In the method of the invention, natural β amyloid peptides can be contacted with a modulator either in vitro or in vivo. Thus, the term "contacted with" is intended to encompass both incubation of a modulator with a natural β-AP preparation in vitro and delivery of the modulator to a site in vivo where natural β-AP is present. Thus, in one embodiment, the methods of the invention for altering β-AP aggregation, and the compounds utilized therein, are used in vitro, for example to detect and quantitate natural β-AP in sample (e.g., a sample of biological fluid). The source of natural β-AP used in the method can be, for example, a sample of cerebrospinal fluid (e.g., from an AD patient, an adult susceptible to AD due to family history, or a normal adult). The natural β-AP sample is contacted with a modulator of the invention and aggregation of the β-AP is measured, such as by as assay described in Example 2. The degree of aggregation of the β-AP sample can then be compared to that of a control sample(s) of a known concentration of β-AP, similarly contacted with the modulator and the results can be used as an indication of whether a subject is susceptible to or has a disorder associated with β-amyloidosis. Moreover, β-AP can be detected by detecting a modulating group incorporated into the modulator. For example, modulators incorporating a biotin compound as described herein (e.g., an amino-terminally biotinylated β-AP peptide) can be detected using a streptavidin or avidin probe which is labeled with a detectable substance (e.g., an enzyme, such as peroxidase). Detection of natural β-AP aggregates mixed with a modulator of the invention using a probe that binds to the modulating group (e.g., biotin/streptavidin) is described further in Example 2.

In a preferred embodiment, the method of the invention for altering natural β-AP aggregation is used therapeutically in the treatment of disorders associated with β amyloidosis, e.g., Alzheimer's Disease. A modulator of the invention can be contacted with natural β amyloid peptides present in a subject (e.g., in the cerebrospinal fluid or cerebrum of the subject) to thereby alter the aggregation of the natural β-AP. The modulator may be administered to a subject by any suitable route effective for inhibiting natural β-AP aggregation in the subject, although in a particularly preferred embodiment, the modulator is administered parenterally, most preferably to the central nervous system of the subject. Possible routes of administration include intraspinal administration and intracerebral administration (e.g., intracerebrovascular administration).

Suitable modes and devices for delivery of therapeutic compounds to the CNS of a subject are known in the art, including cerebrovascular reservoirs (e.g., Ommaya or Rikker reservoirs; see e.g., Raney, J. P. et al. (1988) *J Neurosci. Nurs.* 20:23–29; Sundaresan, N. et al. (1989) *Oncology* 3:15–22), catheters for intrathecal delivery (e.g., Port-a-Cath, Y-catheters and the like; see e.g., Plummer, J. L. (1991) *Pain* 44:215–220; Yaksh, T. L. et al. (1986) *Pharmacol. Biochem. Behav.* 25:483–485), injectable intrathecal reservoirs (e.g., Spinalgesic; see e.g., Brazenor, G. A. (1987) *Neurosurgery* 21:484–491), implantable infusion pump systems (e.g., Infusaid; see e.g., Zierski, J. et al. (1988) *Acta Neurochem. Suppl.* 43:94–99; Kanoff, R. B. (1994) *J Am. Osteopath. Assoc.* 94:487–493) and osmotic pumps (sold by Alza Corporation). A particularly preferred mode of administration is via an implantable, externally programmable infusion pump. Suitable infusion pump systems and reservoir systems are also described in U.S. Pat. No. 5, 368,562 by Blomquist and U.S. Pat. No. 4,731,058 by Doan, developed by Pharmacia Deltec Inc.

The method of the invention for altering β-AP aggregation in viva , and in particular for inhibiting β-AP aggregation, can be used therapeutically in diseases associated with abnormal β amyloid aggregation and deposition to slow the rate of β amyloid deposition and/or lessen the degree of β amyloid deposition, thereby ameliorating the course of the disease. In a preferred embodiment, the method is used to treat Alzheimer's disease (e.g., sporadic or familial AD, including both individuals exhibiting symptoms of AD and individuals susceptible to familial AD). The method can also be used therapeutically to treat other clinical occurrences of β amyloid deposition, such as in Down's syndrome individuals and in patients with hereditary cerebral hemorrhage with amyloidosis-Dutch-type (HCHWA-D). While inhibition of β-AP aggregation is a preferred therapeutic method, modulators that promote β-AP aggregation may also be useful therapeutically by allowing for the sequestration of β-AP at sites that do not lead to neurological impairment.

This invention is further illustrated by the following examples which should not be construed as limiting. A modulator's ability to alter the aggregation of β-amyloid peptide in the assays described below are predictive of the modulator's ability to perform the same function in vivo. The contents of all references, patents and published patent applications cited throughout this application are hereby incorporated by reference.

EXAMPLE 1:

Construction of β-Amyloid Modulators

A β-amyloid modulator composed of an amino-terminally biotinylated β-amyloid peptide of the amino acid sequence:

DAEFRHDSGYEVHHQKLVFFAEDVGSNKGAIIGLMVGGVV (positions 1 to 40 of SEQ ID NO: 1) was prepared by solid-phase peptide synthesis using an $N^{\alpha}$-9- fluorenylmethyloxycarbonyl (FMOC)-based protection strategy as follows. Starting with 2.5 mmoles of FMOC-Val-Wang resin, sequential additions of each amino acid were performed using a four-fold excess of protected amino acids, 1-hydroxybenzotriazole (HOBt) and diisopropyl carbodiimide (DIC). Recouplings were performed when necessary as determined by ninhydrin testing of the resin after coupling. Each synthesis cycle was minimally described by a three minute deprotection (25% piperidine/N-methyl-pyrrolidone (NMP)), a 15 minute deprotection, five one minute NMP washes, a 60 minute coupling cycle, five NMP washes and a ninhydrin test. To a 700 mg portion of the fully assembled peptide-resin, biotin (obtained commercially from Molecular Probes, Inc.) was substituted for an FMOC-amino acid was coupled by the above protocol. The peptide was removed from the resin by treatment with trifluoroacetic acid (TFA) (82.5%), water (5%), thioanisole (5%), phenol (5%), ethanedithiol (2.5%) for two hours followed by precipitation of the peptide in cold ether. The solid was pelleted by centrifugation (2400 rpm×10 min.), and the ether decanted. It was resuspended in ether, pelleted and decanted a second time. The solid was dissolved in 10% acetic acid and lyophilized to dryness to yield 230 mg of crude biotinylated peptide. 60 mg of the solid was dissolved in 25% acetonitrile (ACN) /0.1% TFA and applied to a C18 reversed phase high performance liquid chromatography (HPLC) column. Biotinyl βAP$_{1-40}$ was eluted using a linear gradient of 30–45% acetonitrile/0.1% TFA over 40 minutes. One primary fraction (4 mg) and several side fractions were isolated. The main fraction yielded a mass spectrum of 4556 (matrix-assisted laser desorption ionization-time of flight) which matches the theoretical (4555) for this peptide.

A β-amyloid modulator composed of an amino-terminally biotinylated β-amyloid peptide of the amino acid sequence:

DAEFRHDSGYEVHHQ (positions 1 to 15 of SEQ ID NO: 1) was prepared on an Advanced ChemTech Model 396 multiple peptide synthesizer using an automated protocol established by the manufacturer for 0.025 mmole scale synthesis. Double couplings were performed on all cycles using 2-(1 H-benzotriazol-1-yl)-1,1,3,3 -tetramethyluronium hexafluorophosphate (HBTU)/N ,N-diisopropylethylamine (DIEA)/HOBt/FMOC-AA in four-fold excess for 30 minutes followed by DIC/HOBt/FMOC-AA in four-fold excess for 45 minutes. The peptide was deprotected and removed from the resin by treatment with TFA/water (95%/5%) for three hours and precipitated with ether as described above. The pellet was resuspended in 10% acetic acid and lyophilized. The material was purified by a preparative HPLC using 15%-40 % acetonitrile over 80 minutes on a Vydac C18 column (21× 250 mm). The main isolate eluted as a single symmetrical peak when analyzed by analytical HPLC and yielded the expected molecular weight when analyzed by electrospray mass spectrometry. Result=2052.6 (2052 theoretical).

EXAMPLE 2:

Inhibition of β-Amyloid Aggregation by Modulators

The ability of β-amyloid modulators to inhibit the aggregation of natural β-AP when combined with the natural β-AP was examined in a series of aggregation assays. Natural β-AP (β-AP$_{1-40}$) was obtained commercially from Bachem (Torrance, Calif.). Amino-terminally biotinylated β-AP modulators were prepared as described in Example 1.

A. Optical Density Assay

In one assay, β-AP aggregation was measured by determining the increase in turbidity of a solution of natural β-AP over time in the absence or presence of various concentrations of the modulator. Turbidity of the solution was quantitated by determining the optical density at 400 nm ($A_{400\,nm}$) of the solution over time.

The aggregation of natural β-AP in the absence of modulator was determined as follows. β-$AP_{1-40}$ was dissolved in hexafluoro isopropanol (HFIP; Aldrich Chemical Co., Inc.) at 2 mg/ml. Aliquots of the HFIP solution (87 µl) were transferred to individual 10 mm ×75 mm test tubes. A stream of argon gas was passed through each tube to evaporate the HFIP. To the resulting thin film of peptide, dimethylsulfoxide (DMSO; Aldrich Chemical Co., Inc.) (25 µl) was added to dissolve the peptide. A 2 mm×7 mm teflon-coated magnetic stir bar was added to each tube. Buffer (475 µL of 100 mM NaCl, 10 mM sodium phosphate, pH 7.4) was added to the DMSO solution with stirring. The resulting mixture was stirred continuously and the optical density was monitored at 400 nm to observe the formation of insoluble peptide aggregates.

Alternatively, β-$AP_{1-40}$ was dissolved in DMSO as described above at 1.6 mM (6.9 mg/ml) and aliquots (25 µl) were added to stirred buffer (475 µl), followed by monitoring of absorbance at 400 nm.

For inhibition studies in which a β-amyloid modulator was dissolved in solution together with the natural β-AP, the modulators were dissolved in DMSO either with or without prior dissolution in HFIP. These compounds were then added to buffer with stirring, followed by addition of β-$AP_{1-40}$ in DMSO. Alternatively, HFIP solutions of modulators were combined with β-$AP_{1-40}$ in HFIP followed by evaporation and redissolution of the mixture in DMSO. Buffer was then added to the DMSO solution to initiate the assay. The amino-terminally biotinylated β-amyloid peptide modulators N-biotinyl-β$AP_{1-40}$, and N-biotinyl-β$AP_{1-15}$ were tested at concentrations of 1% and 5% in the natural β-$AP_{1-40}$ solution.

A representative example of the results is shown graphically in FIG. 1, which depicts the inhibition of aggregation of natural β-$AP_{1-40}$ by N-biotinyl-β$AP_{1-40}$. In the absence of the modulator, the optical density of the natural β-AP solution showed a characteristic sigmoidal curve, with a lag time prior to aggregation (approximately 3 hours in FIG. 1) in which the $A_{400\,nm}$ was low, followed by rapid increase in the $A_{400\,nm}$, which quickly reached a plateau level, representing aggregation of the natural β amyloid peptides.

In contrast, in the presence of as little as 1% of the N-biotinyl-β$AP_{1-40}$ modulator, aggregation of the natural β amyloid peptides was markedly inhibited, indicated by an increase in the lag time, a decrease in the slope of aggregation and a decrease in the plateau level reached for the turbidity of the solution (see FIG. 1). N-biotinyl-β$AP_{1-40}$ at a concentration of 5% similarly inhibited aggregation of the natural β amyloid peptide.

Furthermore, similar results were observed when N-biotinyl-β$AP_{1-15}$ was used as the modulator. These results demonstrate that an N-terminally biotinylated β-AP modulator can effectively inhibit the aggregation of natural β amyloid peptides, even when the natural β amyloid peptides are present at as much as a 100-fold molar excess concentration.

B. Fluorescence Assay

In a second assay, β-AP aggregation was measured using a fluorometric assay essentially as described in Levine, H. (1993) *Protein Science* 2:404–410. In this assay, the dye thioflavine T (ThT) is contacted with the β-AP solution. Association of ThT with aggregated β-AP, but not monomeric or loosely associated β-AP, gives rise to a new excitation (ex) maximum at 450 nm and an enhanced emission (em) at 482 nm, compared to the 385 nm (ex) and 445 nm (em) for the free dye. β-AP aggregation was assayed by this method as follows. Aliquots (2.9 µA) of the solutions used in the aggregation assays as described above in section A were removed from the samples and diluted in 200 µl of potassium phosphate buffer (50 mM, pH 7.0) containing thioflavin T (10 µM; obtained commercially from Aldrich Chemical Co., Inc.). Excitation was set at 450 nm and emission was measured at 482 nm. Similar to the results observed with the optical density assay described above in section A, as little as 1% of the N-biotinylated β-AP modulators was effective at inhibiting the aggregation of natural β amyloid peptides using this fluorometric assay.

C. Static Aggregation Assay

In a third assay, β-AP aggregation was measured by visualization of the peptide aggregates using SDS-polyacrylamide gel electrophoresis (SDS-PAGE). In this assay, β-AP solutions were allowed to aggregate over a period of time and then aliquots of the reaction were run on a standard SDS-PAGE gel. Typical solution conditions were 200 µM of β-$AP_{1-40}$ in PBS at 37° C. for 8 days or 200 µM β-$AP_{1-40}$ in 0.1 M sodium acetate at 37° C. for 3 days. The peptide aggregates were visualized by Coomassie blue staining of the gel or, for β-AP solutions that included a biotinylated β-AP modulator, by western blotting of a filter prepared from the gel with a streptavidin-peroxidase probe, followed by a standard peroxidase assay. The β-AP aggregates are identifiable as high molecular weight, low mobility bands on the gel, which are readily distinguishable from the low molecular weight, high mobility β-AP monomer or dimer bands.

When natural β-$AP_{1-40}$ aggregation was assayed by this method in the absence of any β amyloid modulators, high molecular weight aggregates were readily detectable on the gel. In contrast, when N-biotinyl-β-$AP_{1-40}$ modulator self-aggregation was assayed (i.e., aggregation of the N-biotinyl peptide alone, in the absence of any natural β-AP), few if any high molecular weight aggregates were observed, indicating that the ability of the modulator to self-aggregate is significantly reduced compared to natural β-AP. Finally, when aggregation of a mixture of natural β-AP $_{1-40}$ and N-biotinylated β-$AP_{1-40}$ was assayed by this method, reduced amounts of the peptide mixture associated into high molecular weight aggregates, thus demonstrating that the β amyloid modulator is effective at inhibiting the aggregation of the natural β amyloid peptides.

EXAMPLE 3:

Neurotoxicity Analysis of β-Amyloid Modulators

The neurotoxicity of the β-amyloid modulators is tested in a cell-based assay using the neuronal precursor cell line PC-12, or primary neuronal cells, and the viability indicator 3,(4,4-dimethylthiazol-2-yl)2,5-diphenyl-tetrazolium bromide (MTT). (See Shearman, M. S. et al. (1994) *Proc. Natl. Acad. Sci. USA* 91:1470–1474; Hansen, M. B. et al. (1989) *J Immun. Methods* 119:203–210). PC-12 is a rat adrenal pheochromocytoma cell line and is available from the American Type Culture Collection, Rockville, Md. (ATCC CRL 1721). MTT (commercially available from Sigma Chemical Co.) is a chromogenic substrate that is converted from yellow to blue in viable cells, which can be detected spectrophotometrically.

To test the neurotoxicity of a β-amyloid modulator (either alone or combined with natural β-AP), cells first are plated in 96-well plates at 7,000–10,000 cells/well and allowed to adhere by overnight culture at 37° C. Serial dilutions of freshly dissolved or "aged" modulators (either alone or combined with natural β-AP) in phosphate buffered saline (PBS) are added to the wells in triplicate and incubation is continued for two or more days. Aged modulators are prepared by incubating an aqueous solution of the modulator at 37° C. undisturbed for a prolonged period (e.g., five days or more). For the final two hours of exposure of the cells to the modulator preparation, MTT is added to the media to a final concentration of 1 mg/ml and incubation is continued at 37° C. Following the two hour incubation with MTT, the media is removed and the cells are lysed in isopropanol/0.4N HCl with agitation. An equal volume of PBS is added to each well and the absorbance of each well at 570 nm is measured to quantitate viable cells. Alternatively, MTT is solubilized by addition of 50% N,N-dimethyl formamide/20% sodium dodecyl sulfate added directly to the media in the wells and viable cells are likewise quantitated by measuring absorbance at 570 nm. The relative neurotoxicity of a β-amyloid modulator (either alone or in combination with natural β-AP) is determined by comparison to natural β-AP alone (e.g., β1–40, β1–42), which exhibits neurotoxicity in this assay and thus can serve as a positive control.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A β-amyloid peptide compound comprising a formula:

H
  A—N—(Xaa)

wherein Xaa is a β-amyloid peptide having an amino-terminal amino acid residue corresponding to position 668 of β-amyloid precursor protein-770 (APP-770) or to a residue carboxy-terminal to position 668 of APP-770, and A is a modulating group attached to the amino-terminus of the β-amyloid peptide such that the compound inhibits aggregation of natural β-amyloid peptides when contacted with the natural β-amyloid peptides, wherein A comprises a cyclic or heterocyclic moiety.

2. A β-amyloid peptide compound comprising a formula:

O
      ‖
  (Xaa)—C—A wherein Xaa is a β-amyloid peptide and A is a modulation group attached to the carboxy-terminus fo the β-amyloid peptide such that the compound inhibits aggregation of natural β-amyloid peptides when contacted with the natural β-amyloid peptides, wherein A comprises a cyclic or heterocyclic moiety or other moiety having similar steric bulk.

3. The compound of claim 1 or 2, wherein the A group comprises a biotin compound of the formula:

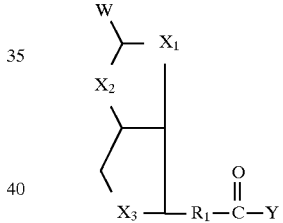

wherein $X_1$–$X_3$ are each independently selected from the group consisting of S, O and NR', wherein R' is selected from the group consisting of hydrogen, an aryl moiety, a lower alkyl moiety, an alkenyl moiety and an alkynyl moiety;

W is =O or N(R')$_2$;

$R_1$ is a lower alkylenyl moiety,

Y is a direct bond or a spacer molecule selected for its ability To react with an amino group, whereby at least one of $X_1$–$X_3$ is an NR' group or W is an N(R')$_2$ group.

4. The compound of claim 1 or 2, wherein the β-amyloid peptide of the compound has an amino-terminal amino acid residue corresponding to position 672 of APP-770, or to a residue carboxy-terminal to position 672 of APP-770.

5. The compound of claim 1 or 2, wherein the β-amyloid peptide of the compound consists of an amino acid sequence:

DAEFRHDSGYEVHHQKLV(Xaa$_{19}$)(Xaa$_{20}$)AEDVGSNKGAIIG-LMVGGVVIAT (SEQ ID NO: 3), wherein Xaa$_{19}$ and Xaa$_{20}$ are each independently selected from the group consisting of phenylalanine, isoleucine, leucine, threonine, serine, alanine, valine and glycine, or an amino-terminal or carboxy-terminal deletion thereof having at least 6 amino acid residues.

6. The compound of claim 1 or 2, wherein the β-amyloid peptide of the compound consists of an amino acid sequence: DAEFRHDSGYEVHHQ (positions 1 to 15 of SEQ ID NO: 3).

7. A β-amyloid modulator compound comprising a retro-inverso isomer of a β-amyloid peptide, wherein the compound inhibits the aggregation of natural β-amyloid peptides when contacted with the natural β-amyloid peptides.

8. The compound of claim 7, wherein The retro-inverso isomer of the β-amyloid peptide further comprises a modulating group attached to the amino-terminal end of the retro-inverso isomer.

9. The compound of claim 7, wherein the retro-inverso isomer of The β-amyloid peptide further comprises a modulating group attached to the carboxy-terminal end of the retro-inverso isomer.

10. The compound of claim 7, wherein the retro-inverso isomer of the β-amyloid peptide further comprises a modulating group attached to the amino-and carboxy-terminal ends of the retro-inverso isomer.

11. The compound of claim 7, which is modified to label the compound with a detectable substance.

12. A pharmaceutical composition comprising a therapeutically effective amount of the compound of claim 7 and a pharmaceutically acceptable carrier.

13. A packaged formulation for treating a subject for a disorder associated with β-amyloidosis, comprising a therapeutically effective amount of the compound of claim 7 packaged with instructions for using the compound for treating a subject having a disorder associated with β-amyloidosis.

14. In an infusion pump, the improvement comprises, the inclusion of a composition of claim 12 in a reservoir for infusion.

15. In a catheter, the improvement comprises, the inclusion of a composition of claim 12 in lumen of the catheter.

16. In a needle, the improvement comprises, the inclusion of a composition of claim 12 in a lumen of the needle.

17. A pharmaceutical composition comprising a therapeutically effective amount of a β-amyloid peptide compound sufficient to inhibit aggregation of natural β-amyloid peptides, the β-amyloid peptide compound comprising a formula:

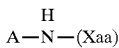

wherein Xaa is a β-amyloid peptide having an amino-terminal amino acid residue corresponding to position 668 of β-amyloid precursor protein-770 (APP-770) or to a residue carboxy-terminal to position 668 of APP-770, and A is a modulating group attached to the amino-terminus of the β-amyloid peptide such that the compound inhibits aggregation of natural β-amyloid peptides when contacted with the natural β-amyloid peptides; and a pharmaceutically acceptable carrier.

18. A pharmaceutical composition comprising:

a therapeutically effective amount of a β-amyloid peptide compound sufficient to inhibit aggregation of natural β-amyloid peptides, the β-amyloid peptide compound comprising a formula:

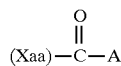

wherein Xaa is a β-amyloid peptide and A is a modulating group attached to the carboxy-terminus of the β-amyloid peptide such that the compound inhibits aggregation of natural β-amyloid peptides when contacted with the natural β-amyloid peptides; and a pharmaceutically acceptable carrier.

19. The pharmaceutical composition of claim 17 or 18, wherein the pharmaceutically acceptable carrier is suitable for parenteral administration.

20. The pharmaceutical composition of claim 17 or 18, wherein the pharmaceutically acceptable carrier is suitable for administration to the central nervous system of a subject.

21. The pharmaceutical composition of claim 17 or 18, wherein the compound is in an amount sufficient to inhibit aggregation of at least a molar excess amount of natural β-amyloid peptides.

22. A packaged formulation for treating a subject for a disorder associated with β- amyloidosis, comprising the compound of claim 1 or 2 packaged with instructions for using the compound for treating a subject having a disorder associated with β-amyloidosis.

23. The packaged formulation of claim 22, wherein the instructions are for using the compound for treating a subject having Alzheimer's disease.

24. In an infusion pump, the improvement comprising the inclusion of the pharmaceutical composition of claim 17 or 18 in a reservoir for infusion.

25. In a catheter, the improvement comprising the inclusion of the pharmaceutical composition of claim 17 or 18 in a lumen of the catheter.

26. In a needle, the improvement comprising the inclusion of the pharmaceutical composition of claim 17 or 18 in a lumen of the needle.

27. The packaged formulation of claim 13, wherein the instructions are for using the compound for treating a subject having Alzheimer's disease.

* * * * *

UNITED STATES PATENT AND TRADEMARK OFFICE
CERTIFICATE OF CORRECTION

PATENT NO. : 5,817,626
DATED : October 6, 1998
INVENTOR(S) : Mark A. Findeis et al.

It is certified that error appears in the above-identified patent and that said Letters Patent is hereby corrected as shown below:

At column 19, line 58, delete "modulation" and insert --modulating--.

At column 19, line 59, delete "fo" and insert --of--.

At column 20, line 51, delete "To" and insert --to--.

At column 20, line 60, delete "(Zaa$_{19}$)" and insert --(Xaa$_{19}$)--.

At column 21, line 9, delete "The" and insert --the--.

At column 21, line 14, delete "The" and insert --the--.

At column 21, line 36, before the word "lumen", please insert --a--.

Signed and Sealed this

Sixteenth Day of February, 1999

Attest:

*Acting Commissioner of Patents and Trademarks*

*Attesting Officer*